United States Patent
Hager

(10) Patent No.: US 6,887,666 B1
(45) Date of Patent: May 3, 2005

(54) METHODS FOR IDENTIFICATION OF IDENTICAL NUCLEIC ACID FRAGMENTS FROM DIFFERENT NUCLEIC ACID POPULATIONS

(75) Inventor: Joerg Hager, Mennecy (FR)

(73) Assignee: Integragen, Evry (FR)

( * ) Notice: Subject to any disclaimer, the term of this patent is extended or adjusted under 35 U.S.C. 154(b) by 0 days.

(21) Appl. No.: 09/936,299

(22) PCT Filed: Mar. 9, 2000

(86) PCT No.: PCT/EP00/02053

§ 371 (c)(1),
(2), (4) Date: Dec. 20, 2001

(87) PCT Pub. No.: WO00/53802

PCT Pub. Date: Sep. 14, 2000

(30) Foreign Application Priority Data

Mar. 12, 1999 (DE) .......................... 199 11 130

(51) Int. Cl.[7] .............................. C12Q 1/68; C12P 19/34
(52) U.S. Cl. ............................... 435/6; 435/91.2
(58) Field of Search .................... 435/6, 91.1, 91.2, 435/183; 536/23.1, 23.5, 24.1, 24.3, 24.33

(56) References Cited

U.S. PATENT DOCUMENTS

| | | | | |
|---|---|---|---|---|
| 5,376,526 A | * | 12/1994 | Brown et al. ................. | 435/6 |
| 5,750,335 A | | 5/1998 | Gifford ......................... | 435/6 |
| 5,879,886 A | | 3/1999 | Meo et al. .................... | 435/6 |
| 6,150,112 A | * | 11/2000 | Weissman et al. ........... | 435/6 |
| 6,287,825 B1 | * | 9/2001 | Weissman et al. ......... | 435/91.2 |
| 6,372,434 B1 | * | 4/2002 | Weissman et al. ........... | 435/6 |
| 6,524,794 B1 | * | 2/2003 | Grant et al. .................. | 435/6 |
| 6,573,053 B1 | * | 6/2003 | Firth et al. ................... | 435/6 |

FOREIGN PATENT DOCUMENTS

| | | |
|---|---|---|
| WO | WO 89/12695 | 12/1989 |
| WO | WO 93/22457 | 11/1993 |
| WO | WO 93/22462 | 11/1993 |
| WO | WO 95/12688 | 5/1995 |
| WO | WO 95/12689 | 5/1995 |
| WO | WO 96/17082 | 6/1996 |
| WO | WO 96/23903 | 8/1996 |
| WO | WO 96/41002 | 12/1996 |
| WO | WO 99/25872 | 5/1999 |

OTHER PUBLICATIONS

Green et al. (PNAS (1990) 87: 1213–1217).*
Klein et al., 96 Proc. Nat'l. Acad. Sci. 4494–99 (1999).
Lishanski et al., 91 Proc. Nat'l. Acad. Sci. 2674–78 (1994).
Cheung et al., 47 GENOMICS 1–6 (1998).
McAllister et al., 47 GENOMICS 7–11 (1998).
Smith et al., 93 Proc. Nat'l. Acad. Sci. 4374–79 (1996).

* cited by examiner

Primary Examiner—Kenneth R. Horlick
(74) Attorney, Agent, or Firm—Preston Gates Ellis & Rouvelas Meeds LLP

(57) ABSTRACT

The present invention relates to genetic mapping of complex quantitative and qualitative traits. This invention more particularly relates to methods to identify identical DNA fragments from two different DNA sources. The method allows the amplification of the DNAs, their, labelling, and the separation of perfectly matched DNAs from imperfectly matched DNAs or from DNAs formed through hybridisation from the same source (e.g., homohybrids). The invention can be used to identify genes or gene mutations, which are relevant to pathological conditions or particular traits.

14 Claims, No Drawings

METHODS FOR IDENTIFICATION OF IDENTICAL NUCLEIC ACID FRAGMENTS FROM DIFFERENT NUCLEIC ACID POPULATIONS

CROSS REFERENCE TO RELATED APPLICATION

The present application is the national stage and claims, under 35 U.S.C. § 371, the benefit of PCT/EP00/02053, filed Mar. 9, 2000, which claims priority to Federal Republic of Germany Application 199 11 130.8, filed Mar. 12, 1999.

FIELD OF INVENTION

The present invention relates to the field of genomics and genetic analysis, more particularly to genetic mapping of complex quantitative and qualitative traits. More particularly, the present invention provides compositions and methods to analyze genetic information from different sources in order to identify relevant therapeutic genes or mutations. This invention more particularly relates to compositions and methods to identify identical DNA fragments from different DNA sources. The method allows the separation of perfectly matched DNA's from imperfectly matched DNA's or from DNA's formed through hybridisation from the same source (e.g., homohybrids). The method represents alternative and/or improved variants of Genomic Mismatch Scanning (GMS), and provides significant improvements over the GMS procedure, allowing working with small starting amounts of DNA, specific amplification, decreased cost and decreased number of reaction steps.

BACKGROUND

A major challenge for biology and medicine today is the identification of genes implicated in common, complex, human diseases like asthma, type 2 diabetes mellitus, obesity etc. The identification of such genes is usually carried out performing linkage and/or association studies in large family or patient samples. These studies can be performed using a variety of genetic markers (sequences in the genome which differ between individuals i.e. that are polymorph). The most widespread polymorphisms used are microsatellite markers consisting of short, specific repeat sequences or single nucleotide polymorphisms (SNP's) that differ in just one nucleotide. Different analysis technologies have been developed to genotype these markers like, gel-based electrophoresis, DNA hybridisation to an ordered array, identification using mass spectrometry.

The major goal of genetics is to link a phenotype (i.e. a qualitative or quantitative measurable feature of an organism) to a gene or a number of genes. Historically there are two genetic approaches that are applied to identify genetic loci responsible for a phenotype, familial linkage studies and association studies. Whatever the approach is, genetic studies are based on polymorphisms, i.e. base differences in the DNA sequence between two individuals at the same genetic locus. The existence of sequence differences for the same genetic locus is called allelic variation. It has long been known that different alleles of a gene can result in different expression of a given phenotype.

Linkage analysis has been the method of choice to identify genes implicated in many diseases both monogenic and multigenic, but where only one gene is implicated for each patient. Linkage analysis follows the inheritance of alleles in a family and tries to link certain alleles to a phenotype (e.g. a disease). In other terms one seeks for shared alleles between individuals with the same phenotype that are identical by descent (IBD) i.e. are derived from the same ancestor. In order to be reasonably powerful in the statistical analysis, the studied polymorphisms have to fulfil several criteria:

high heterozygosity i.e. many alleles exist for a given locus (this increases the informativity);
genome wide representation;
detectable with standard laboratory methods.

A type of polymorphisms fulfilling most of these criteria is a microsatellite marker. These are repetitive sequence elements of two (e.g. CA), three or four bases. The number of repetitions is variable for a given locus, resulting in a high number of possible alleles i.e. high heterozygosity (70–90%). They are widely distributed over the genome. Today almost 20.000 microsatellite markers have been identified and mapped (coverage app. 0.5–2 Mbases).

Microsatellite markers are still the genetic markers of choice for linkage analyses. Genotyping of these markers is performed by amplifying the alleles by PCR and size separation in a gel matrix (slab gel or capillary).

For the study of complex human diseases usually 400–600 microsatellite markers are used that are distributed in regular distances over the whole genome (about every 10–15 mega bases).

The advantages of familial linkage studies include established, well mapped marker systems (microsatellite markers); statistical analysis tools are relatively well developed; high informativity; allow the parallel dissection of several loci involved in a genotype (meta-analysis); well developed comparative maps between species.

Disadvantages of familial linkage studies include the Expensive aspect (Many PCR's, allele scoring is labor intensive, fluorescent marker labelling); slow because although some multiplexing can be achieved high parallelization is not possible (no microsatellite DNA chips); statistical power limited to dissect small effects; results are dependent on allele frequencies and heterozygosity; extensive family collections with affected individuals are necessary (200–2000 individuals); IBD regions usually extend over large regions unsuitable for direct gene cloning, often 10–15 mega bases (low resolution).

Another approach to genetic analysis relies on association studies. Linkage studies follow alleles in families. However, each family might have a different allele of a genetic locus linked to the phenotype of interest. Association studies, in contrast, follow the evolution of a given allele in a population. The underlying assumption is that at a given time in evolutionary history one polymorphism became fixed to a phenotype because:

a) it is itself responsible for a change in phenotype or;
b) it is physically very close to such an event and is therefore rarely separated from the causative sequence element by recombination (one says the polymorphism is in linkage disequilibrium with the causative event).

This is a fundamental difference between linkage and association. Whereas in a genetically acquired trait there must be linkage of a sequence to the causative allele if one could perform an infinitely dense linkage experiment, there is no a priori reason that there might be a single (or very few) causative allele(s) in the population (i.e. there is association). This has major implications for the statistical analysis. An example for linkage without association are many monogenic diseases e.g. maturity onset diabetes of the young (MODY) where almost each family carries a different mutation in the same gene. The gene was identified through linkage studies. Association studies would have failed to identify the locus. As association studies postulate the existence of one given allele for a trait of interest one wants the markers for an association study to be simple. The markers of choice for these studies are accordingly single nucleotide polymorphisms (SNP's). These polymorphisms show a simple base exchange at a given locus (i.e. they are bi-rarely tri-allelic). Association studies can be carried out either in population samples (cases vs. controls) or family samples (parents and one offspring where the transmitted alleles constitute the "cases" and the non-transmitted the "controls"). The main advantages of association studies using SNP's are:

- relatively easy to type (any technology allowing single base discrimination e.g. DNA chips, mass spectrometry);
- SNP's are very abundant in the human genome (on average one SNP every 300–1000 bases);
- Association allows defining a relatively well-delimited genetic interval (usually several kilo bases).

Disadvantages are:

- associations may only be detected at very high resolutions (unsuitable high number of SNP's must be screened, probably >100.000).
- as association cannot be postulated to exist a priori, the statistic rules for multiple testing apply i.e. the result for each additional SNP tested must be corrected for. The result is an unsuitable high threshold for positive association when thousands of markers are tested or in other words an inflation of false positive results at nominal significance levels. New statistical tools are needed;
- association tests are usually carried out as two by two tests (i.e. polymorphisms at a given locus are tested against a phenotype). Meta-analyses are difficult if not impossible to carry out for thousands of markers;
- like linkage, association analysis is influenced by allele frequency;
- integrated genetic maps for SNP's don't exist yet;
- large sample collections are needed;
- current technology is too expensive to genotype thousands of samples for thousands of SNP's (PCR, costs of chip technology, instrumentation) and discrimination is still not reliable enough (e.g. Affymetrix SNP chip).

Accordingly, there is a need for improved or alternative genetic analysis methods that would overcome the drawbacks of these prior art technologies. In this regard, the ideal genotyping technology should be capable of looking for both linkage and association and, at the same time, avoid the disadvantages of these methods. It should be reliable, allow genome wide analysis, be capable of restraining phenotype-linked loci to small intervals, and be simple to perform and analyze and be cheap.

A method called genomic mismatch scanning ("GMS") seems to fulfill most of these requirements. Genomic mismatch scanning was developed in the "mismatch repair community" which had little to do with the human linkage community trying to find the genes involved in human traits. More particularly, in 1993 Nelson SF et al. (Genomic mismatch scanning: A new approach to genetic linkage mapping. *Am J Hum Genet*. 61:111–119 (1993)) described a method that allowed the detection and quantification of the relationship between different strains of yeast. The method consists of mixing the DNA's from different yeast strains and destroying everything that is not identical using a set of mismatch repair enzymes. Apart from the research community is working on mismatch repair the article had no major impact. However, it seemed logical that this technology could also be applied to detect identical regions in humans. In this regard, Linda McAllister et al. published in 1998 a proof-of-principle article where they described the identification of a human disease locus on chromosome 11 using GMS (Linda McAllister, Lolita Penland and Patrick O. Brown. Enrichment of loci identical by descent between pairs of mouse or human genomes by genomic mismatch scanning, *Genomics* 47:7–11 (1998)).

Briefly the method consists of the following steps:

restriction of the DNA from two individuals;

labeling one of the DNA's by methylation;

mixing of the two DNA's thereby creating a mixture of heteroduplexes between the two DNA's, which are hemimethylated, and homoduplexes of the original DNA's derived through renaturation of each individuals DNA with itself. As the DNA of one individual was completely methylated and the other non-methylated the resulting homoduplexes are also methylated or non-methylated;

the non-informative homoduplexes are eliminated by several enzymatic steps involving restriction enzymes that only digest fully methylated or fully unmethylated DNA and a final digestion of the DNA by Exo III nuclease.

The remaining heteroduplexes which were formed between the DNA's from the two individuals consist of few fragments which are 100% identical in their sequence composition (the fragments of interest) and those which, due to the heterogeneity between individuals, show sequence differences (i.e. bases are mismatched at those sites);

The mismatched DNA fragments are eliminated by using an enzymatic DNA mismatch repair system consisting of three proteins (mut S, mut H, mut L) which recognize these mismatches and cut the DNA strands at a specific recognition sequence (GATC), the remaining 100% identical DNA heterohybrids can then be identified by specific PCR amplification where the presence or absence of an amplification product is scored.

The advantages of the method over the classical linkage and association studies are:

the method allows unambiguous detection of IBD fragments between individuals, as it is not dependent on allele frequencies or marker heterozygosity;

the method is not limited on the use of polymorphic markers. Any sequence can be used for scoring as long as some sequence and mapping information is available;

no allele discrimination is necessary. The detection signal is digital (i.e. presence or absence of a fragment);

the detection method can be scaled to any density;

due to the unambiguous IBD detection and independence of allele frequency, fewer individuals have to be screened (e.g. 100 sib-pairs give the same power to detect regions of linkage as 400–600 sib-pairs in the classical linkage analysis).

The classical GMS methodology has, however, some disadvantages that make its use as a routine tool for genetic screening difficult:

the amount of DNA for a single experiment is large due to the loss of material throughout the procedure. Usually 5 μg of DNA are needed. Depending on the extraction method this often constitutes more than half the DNA available in a collection;

the methylation of one of the DNA's is not 100% efficient i.e. some of the heteroduplexes can not be distinguished and are lost and some of the homoduplexes of the "methylated" individuals DNA will actually be hemimethylated after the hybridization step and therefore result in background at the detection level (as the DNA from one individual is a priori 100% identical with itself);

as exo III nuclease digestion plays a central part in the technology, only restriction enzymes creating 3' sticky ends can be used for the initial digestion of the DNA (typically Pst I is employed). These enzymes are rare and restrict the choice for the restriction of the DNA and therefore the constitution of the created fragments;

efficient recognition of non-identical, mismatched DNA sequences by the mut SHL system relies on the presence of the recognition sequence GATC in a given fragment. Absence of the sequence results in background signal due to non-eliminated mismatched DNA;

the labeling of one of the DNA's by methylation allows only a two by two pair-wise comparison between different DNA's.

Thus, there is a need in the art for genetic analysis techniques and compounds that are more convenient, easy to perform, reliable and applicable to broader populations of genetic material.

SUMMARY OF THE INVENTION

The present invention now provides novel genetic analysis methods that overcome the drawbacks of the prior art GMS technique. In specific embodiments, the invention discloses alternative and/or improved variants based on the concept of GMS that circumvents most of the disadvantages of the classical approach mentioned above.

More particularly, a method is provided which allows the identification of identical DNA sequences from different sources from a small initial amount of genomic DNA.

A method is also provided to amplify nucleic acids from different populations with a primer comprising a label specific to each population.

A method is also provided to identify genomic DNA regions that are relevant to pathological conditions or particular traits.

A method is also provided for preparing heterohybrid nucleic acid molecules from two or more nucleic acid populations, comprising an amplification step of each nucleic acid population prior to a hybridisation step, the amplification preferably comprising the coupling of an adaptor molecule to each nucleic acid in the populations, more preferably at both ends thereof, and performing an amplification using a primer comprising at least a sequence region that is complementary to a sequence region of the adaptor molecule.

A particular aspect of this invention resides more specifically in a method of separating identical DNA fragments from complex mixtures of at least two nucleic acid populations (from different sources), identical heterohybrids formed, wherein the nucleic acid populations comprise amplified nucleic acids.

More particularly, an object of the present invention resides in a method for the identification (or isolation or separation) of identical nucleic acid fragments from a mixture of at least two nucleic acid populations from different sources, comprising: a) separate digestion of the nucleic acids of said at least two populations with at least one restriction enzyme; b) ligation of specific adaptor sequences to the restriction fragments; c) amplification of the adaptor-ligated restriction fragments generated in a) and b) using adaptor-specific primers; d) hybridisation of the amplification products from the different nucleic acid populations with each other; e) identification (or isolation or separation) of the identical, fully matched, heterohybrid fragments.

This method is advantageous since it allows the amplification of the DNA's (i.e., the use of small amounts of starting material) and the selection of heteroduplexes without methylation prior to the mismatch repair selection (i.e., without restriction regarding restriction enzymes).

A method is also provided to identify DNA regions that are relevant to pathological conditions or particular traits comprising hybridizing at least two nucleic acid populations from different sources having the particular trait or pathology, and separating the identical heterohybrids formed which contain DNA regions that are relevant to said pathological conditions or particular traits, wherein the nucleic acid populations comprise amplified and/or pre-selected nucleic acids.

Other aspects of the present invention reside in compositions, kits, and diagnostic assays.

DETAILED DESCRIPTION OF THE INVENTION

As indicated above, the present invention provides a method for the identification (or isolation or separation) of identical nucleic acid fragments from a mixture of at least two nucleic acid populations, comprising: a) separate digestion of the nucleic acids of said at least two populations with at least one restriction enzyme; b) ligation of a specific adaptor sequence to the restriction fragments; c) amplification of the adaptor-ligated restriction fragments generated in a) and b) using an adaptor-specific primer; d) hybridisation of the amplification products from the different nucleic acid populations with each other; and e) identification (or isolation or separation) of identical, fully matched, heterohybrid fragments.

The invention can be used to analyze various nucleic acid populations, especially with the objective to identify (or separate) identical regions present therein. Typically, the nucleic acid populations are genomic DNA, in particular mammalian genomic DNA such as human genomic DNA. In a preferred embodiment, the nucleic acid populations are human genomic DNA from different subjects that share a trait of interest, in particular a phenotype or pathology. In this embodiment, the method of the present invention is directed at identifying genetic markers of the pathology, or genes (mutations) involved in or responsible for pathology.

The nucleic acid populations may also be genomic DNA from other mammalian species, such as bovine, ovine, canine, sheeps, goats, and the like. In particular, the genomic DNA may be prepared from animals (of the same species) sharing a particular trait (high meat, high milk production, etc.).

The nucleic acid populations may also be genomic DNA from other sources, including prokaryotic (bacteria, pathogenic organisms, etc.), lower eukaryotic (yeasts, etc.), plants, viruses, and the like.

While the nucleic acid population may comprise the total genomic DNA of a cell (or tissue or organism), or a complete genomic library, for instance, it should be noted that a screening or a selection of the starting nucleic acids might also be performed. In particular, the nucleic acid population may be an isolated chromosome (or group of chromosomes).

In performing the instant invention, two or more nucleic acid populations can be used, originating from different sources. In preferred embodiments, 2 to 10 nucleic acid populations are used.

In the first (optional) step, the nucleic acid populations are separately digested to provide restriction fragments. The term "separately" indicates that each population is individually subjected to the digestion, i.e., without being mixed together. One or several restriction enzymes may be used. Preferably, the same restriction enzyme(s) are used for each nucleic acid population. The restriction enzyme(s) can be chosen according to practical considerations, such as size of the generated fragments, specificity for DNA species, enzymatic activity, ease of use, etc. In a preferred embodiment, the restriction enzyme provides, on an average, medium length restriction fragments, more particularly fragments between 2 and 10 kilo bases (kb). Such restriction enzymes include for instance six base recognition site enzymes like Apa I (~2 kb), Bam HI (~5 kb), Bgl I+II (~3 kb), Hind III (~4 kb), Nar I (~4 kb), Sma I (~4 kb) or Xba I (~5 kb).

In a specific embodiment, one single restriction enzyme is used, that provides, on an average, restriction fragments of between 2 and 10 kilo bases.

In a particular embodiment, the restriction fragments can be selected prior to the subsequent ligation and/or amplification step. In particular, the restriction fragments can be size-selected to allow a uniform amplification of all fragments. Size selection may be performed on a gel or by any other technique. On an agarose gel, the restriction fragments are size separated in an electric field beside a size standard for orientation. Fragments in the preferred size range can be cut from the gel and be extracted from the agarose using standard methods (e.g. "Quiaex II", a gel extraction kit from Quiagen AG, Germany). Size separation can also be achieved using column separation with a sieving material like polyacrylamide, sephadex etc.

In addition, the restriction fragments may be cloned into any suitable vector, prior to the amplification step. The vector may be any plasmid, phage, virus, cosmid, artificial chromosome (YAC, BAC), etc. In particular, the restriction fragments may be cloned in a chromosome- and sequence-specific manner. In a particular embodiment, the method thus comprises (i) separate digestion of the nucleic acid populations (e.g., genomic DNA from at least two different sources) and (ii) cloning of (certain) restriction fragments into a vector, in a chromosome- and sequence-specific manner (e.g., through homologous recombination). This cloning step can be used to select certain fragments for further analysis, without analysing the entire DNA population.

Another particular aspect of this invention resides in the use of adaptor molecules that facilitate specific amplification of the nucleic acids and specific treatment of the samples to increase the selectivity of the identification method.

Adaptor molecules are preferably short double stranded DNA fragments (or oligonucleotides) with known sequence composition. More preferably, the adaptor molecules are 5–100 base pair long double stranded DNA molecules, even more preferably 5–50 base pair long. The adaptor molecules allow the introduction of sequence features that greatly improve the genetic analysis procedure. More particularly, the introduction of these adaptors has the following advantages:

the DNA can be amplified by PCR prior to the genetic analysis (e.g., GMS) procedure allowing starting off with less material (100–500 ng). Only one amplification per experiment, using a single primer sequence is necessary, making this method cheap;

the adaptor sequence is preferably designed to include the mut HL recognition sequence (GATC), allowing all mismatched fragments to be removed from the mixture, thereby increasing the selectivity and reducing the background signal the adaptor molecule may also comprise a recognition site for a restriction enzyme that creates 3' sticky ends, such as Aat III.

In a preferred embodiment, the adaptor molecule is a 5–100 base long (double-stranded) oligonucleotide comprising at least one GATC motif.

The adaptor molecules can be prepared according to conventional techniques (artificial synthesis) and ligated to the restriction fragments (or to the nucleic acid population, where no restriction step is conducted), by conventional methods (using for instance a ligase enzyme, such as T4 ligase). The method of this invention preferably comprises the ligation of all of the nucleic acids in the various populations to the same adaptor molecule. More preferably, ligation of the adaptor molecule results in DNA fragments that carry an adaptor sequence at both ends.

Amplification of the nucleic acids (or restriction fragments) may be accomplished by polymerase chain reaction (PCR), according to conventional techniques. Preferably, the amplification is carried out by polymerase chain reaction using a high fidelity, long-range DNA polymerase. Examples of such polymerases include Pfx polymerase (Life Technologies) and Z-Taq polymerase (TaKaRa). Several amplification cycles may be performed, more particularly from 25 to 40.

Another advantage of the instant invention resides in the use of particular primers for the amplification reaction. The primers are preferably complementary to at least part of the adaptor molecule. The primers can be any oligonucleotide, preferably having 5 to 30 bases, even more preferably 5–20 bases. The portion of the primer that is complementary to the (portion of the) adaptor molecule should preferably comprise at least 5, more preferably at least 10 bases, to ensure sufficient selectivity. Primers can be produced by the skilled person according to conventional techniques known in the art (preferably artificial nucleic acid synthesis).

In a preferred embodiment, the primers are labelled, which provides further advantages to the present method. In particular, the introduction of labelled primers for (PCR) amplification allows distinguishing the different DNA populations that are mixed. Indeed, the primer used to amplify each nucleic acid population may exhibit a different label, such as different unique 5' sequences (or some may be labelled and some not), allowing distinguishing the amplified products from each source. This avoids the need for any methylation step. Accordingly, no methylation-specific restriction enzymes are needed and a significant decrease of the cost per experiment can be obtained. Furthermore, the use of labelled primers makes it possible to carry out more than pair-wise comparisons (several individuals included in a reaction, i.e., more than two nucleic acid populations). This can be used to increase the resolution of the method (smaller IBD regions are detected). This feature is especially useful when searching for allelic association.

Moreover, the primers can be designed in a way that allows the exo III nuclease to attack homoduplexes formed upon hybridisation between the nucleic acid populations, but not the heteroduplexes. Accordingly, the restriction ends play no part in the choice of the restriction enzyme for digestion of the nucleic acid populations. The enzymes can thus be chosen according to practical considerations (size of the generated fragments, specificity for DNA species, enzymatic activity and ease of use).

Primers can be labelled by (i) adding a unique 5'-sequence to each primer, (ii) adding a chemical activity to the primer which provides a means to distinguish between the amplification products from different DNA sources and (iii) adding modified nucleotides into the primer allowing to distinguish between the amplification products from different DNA sources. Preferred labelling technique comprises the introduction of a unique 5' sequence to each set of primers.

The identification (or isolation or separation) of the identical, fully matched, heterohybrid fragments can be performed in several ways. Preferably, the identification comprises the following steps (i) separation of homohybrids from heterohybrids; (ii) (identification and) elimination of mismatched heterohybrids, and iii) identification (or isolation or separation) of the identical heterohybrid fragments.

The heterohybrids can be separated from the homohybrids based on labelling of primers, as described above. In particular, the separation may be performed based on the use of primers with a unique 5' end sequence for each nucleic acid population. According to this embodiment, homohybrids only will be blunt ended, i.e., comprise perfectly matched DNA ends (the unique 5' end sequence of the specific primer). Accordingly, all homohybrids can be eliminated by treatment of the hybridisation product with an enzyme that specifically digest blunt-ended double stranded DNA fragments, such as Exo III. Treatment with Exo III results in the formation of single-strands, which can be eliminated through various methods, such as through binding to a single strand-specific matrix.

In this regard, in a specific embodiment, the method of the present invention comprises a) separate amplification of the restriction fragments from different sources using a primer with a unique 5' sequence for each DNA source; b) mixing the amplification products from said different sources carrying unique 5' ends; c) denaturation and rehybridizing said DNA's; d) digesting perfectly matched (blunt ended) DNA's (homoduplexes) by Exo III and e) elimination of the Exo III created single strands through binding to a single strand specific matrix.

The separation of DNA homoduplexes from DNA heteroduplexes may also be performed based on the methylation of one of the two nucleic acid preparations (or restriction fragments). Although not preferred, this embodiment can be performed advantageously where the amplification primer or the adaptor molecule comprises a site of recognition of an enzyme that creates 3' sticky ends (such as Aat III). Indeed, in this embodiment, the nucleic acid populations may be digested with any type of restriction enzyme.

Mismatched heterohybrids may be preferably eliminated with mismatch repair enzymes. In particular, the distinction between (or elimination or separation of) mismatched and perfectly matched nucleic acid fragments can be performed using mismatch repair enzymes mutS, mutL and/or mutH, or derivatives or homologues thereof. Derivatives include fragments or variants of the Mut proteins, i.e., any polypeptide or fragment derived there from and retaining the biological activity of the protein. Preferred derivatives retain at least 80% of the primary structure of the Mut protein. Homologues include proteins exhibiting the same type of enzymatic activity in other biological systems (yeasts, plants, etc.).

In particular, mismatched nucleic acid fragments can be eliminated by (i) incubating the hybridisation mixture with MutS (which binds mismatch) and contacting the resulting product with a MutS-binding material (e.g., support, bead, column, etc.).

Mismatched nucleic acid fragments can also be eliminated by incubating the hybridisation mixture with MutS, MutL and MutH, resulting in a specific cleavage of mismatched hybrids and subsequent formation of blunt ends, which can be eliminated by treatment with particular enzymes (such as exo III) and elimination of single-strand DNA formed.

In a more specific embodiment, the method comprises:
separate digestion of the genomic DNA's from at least two different sources with a restriction enzyme;
ligation of an adaptor molecule to these genomic restriction fragments;
amplification of the adaptor-ligated restriction fragments (preferably by polymerase chain reaction (PCR)), using labelled adaptor-specific primers;
hybridisation of the amplification (e.g., PCR) products from the different DNA sources with each other;
separation of homoduplexes from heteroduplexes;
identification and elimination of mismatched heterohybrids using the mut SHL proteins;
identification of the 100% identical heteroduplex fragments.

As indicated before, the primers have a sequence that is complementary to at least a part of the adaptor sequence. Furthermore, they are preferably labelled, thereby providing a means to distinguish between the amplification products from different DNA sources.

In another aspect, the invention resides in a method of genetic analysis comprising: a) digestion of DNA from different sources which share a common trait of interest, which trait is suspected to be based on the same genetic change, with an enzyme that, on average, provides medium length DNA fragments (e.g., fragments between 2 to 10 kilo bases); b) ligation of specific adaptors to these restriction fragments (these adaptors provide a means to introduce a known sequence and a means for later selection in the reaction); c) labelling of at least one of the DNA's from said different sources with a method that allows to distinguish the DNA's from different sources from each other; d) amplification of the so prepared restriction fragments by polymerase chain reaction (PCR); e) mixing the DNA's from different sources and formation of heteroduplexes between the DNA strands from these sources; f) elimination of homoduplexes formed by the renaturation of two DNA strands from the same source; g) elimination of heteroduplexes which have mismatched bases; h) detection and identification of the resulting 100% identical DNA sequences.

As mentioned above, in a preferred embodiment of the invention, the adaptor molecule includes specific sequence features: a) the recognition site for mut HL (GATC), b) a recognition site for a restriction enzyme creating 3' sticky ends (e.g. aat III).

In another specific embodiment of the present invention one of the DNA's taking part in the procedure is methylated after digestion and adaptor ligation, preferably by using dam methylase. The DNA's from different sources are then separately amplified by PCR using adaptor-specific oligonucleotide primers. The resulting amplification products are digested with a restriction enzyme creating 3' sticky ends (at least 2 sites/fragment introduced into the adaptor) to protect the fragments from exo III digestion. The DNA fragments from two different sources are then mixed and hemi-methylated heteroduplexes are formed between the DNA strands by heat denaturation and renaturation under stringent conditions (Casna et al. (1986) genomic analysis II, isolation of high molecular weight heteroduplex DNA following methylase protection and formamide PERT hybridization Nucleic Acids Res. 14: 7285–7303). Non-methylated and fully methylated homoduplexes are cut by methylation sensitive restriction enzymes. The cut fragments are then further digested by exo III exonuclease and the resulting single stranded regions are eliminated from the reaction mix using some single strand specific matrix known to those skilled in the art (e.g. BND cellulose beads). The remaining heteroduplexes are a mix of fragments, which, are 100% matched and those that have DNA base pair mismatches (due to the difference between individuals). DNA fragments having mismatched DNA sequences are recognized and cut by adding the mut SHL mismatch repair proteins to the reaction mix. Fragments that were cut are further digested by exo III exonuclease and single strands are eliminated as described above.

In a preferred embodiment of the invention the method is characterized by the following steps: a) digestion of DNA from at least two different sources with a restriction enzyme; b) ligation of specific adaptors to the restriction fragments; c) separate amplification of the restriction fragments from the different sources using a primer with a different label (e.g., a unique 5' end) for each DNA of said sources; d) mixing the amplification products from different sources carrying a unique label (e.g., a unique 5' end); e) denaturation and re-hybridisation of said DNA's from different sources; f) digestion of perfectly matched (blunt ended) DNA's (homoduplexes) by exo III exonuclease; g) elimination of the exo III created single strands through binding to a single strand specific matrix; h) recognition and nicking of mismatched heteroduplexes by adding the mut SHL proteins to the reaction mix; i) exo III digestion of nicked DNA's; j) elimination of the exo III created single strands through binding to a single strand specific matrix; k) detection and identification of the remaining 100% matched sequences in the reaction mix.

The identified (or separated or isolated) identical DNA fragments can be further analysed to determine a gene, mutation, and the like. More particularly, the fragments can be analysed by sequencing. They can also be analysed by hybridisation with ordered DNA array(s) or coded beads carrying specific DNA sequences.

The invention also relates to kits that can be used to perform the above described genetic analysis techniques. In particular, the invention resides in a kit suitable for genetic analysis as described above, comprising a double stranded adaptor molecule, a specific labelled primer and, optionally, control DNA's and enzymes. Kits of this invention may further comprise a means for the detection of the selected DNA fragments, preferably an ordered DNA array or coded beads carrying specific DNA sequences.

The invention can be used to identify gene or mutations involved in pathology, such as complex pathologies (obesity, asthma, cardiovascular diseases, CNS disorders, etc.). The invention is broadly applicable to the analysis of any genetic material, especially with the objective of identifying (or screening) identical DNA regions present in two (or more) different nucleic acid populations.

Further aspects and advantages of the present invention will be disclosed in the following experimental section, which should be regarded as illustrative and not limitative.

EXAMPLES

Example 1

Identification of Disease-Related Loci in Related Human Individuals

Genomic DNA from at least two related individuals, with the same disease phenotype, is extracted by standard methods, e.g., phenol-chlorophorme extraction. The DNAs are separately cut with a restriction enzyme (e.g., Bam HI) to create restriction fragments with an average size around 4 kilobases. To these restriction fragments a solution containing short double stranded oligonucleotides (adaptors) is added. The adaptor molecules have sequence ends complementary to the restriction site sequences to allow ligation. The adaptors are then ligated to the restriction fragments from the genomic DNAs using a common ligase (e.g., T4 ligase). The sequence of the adaptors has been chosen in a way that: a) the sequence includes the recognition site for mut HL, b) adapter dimers formed through autoligation of two adaptor molecules are self-complementary and don't compete for primers with the genomic ligation products during PCR. The adaptor carrying fragments are then, separately for each individual, amplified by PCR using primers that are complementary to a part of the adaptor sequence and that carry unique 5' ends. After several rounds of amplification the PCR products of different individuals differ by their ends in respect to each other. The amplification products are then mixed, heat denatured and allowed to re-anneal using stringent hybridisation conditions (Casna et al. (1986) genomic analysis II, isolation of high molecular weight heteroduplex DNA following methylase protection and formamide PERT *Hybridization Nucleic Acids Res.* 14: 7285–7303). This results in the formation of heteroduplexes from the DNAs from different sources (individuals) with forked (single stranded) ends because of the non-complementarity of the primer sequences. In addition homoduplexes are formed by renaturation between the strands of one individual with itself. These homoduplexes are blunt-ended. To this mixture a solution containing exo III (or an equivalent 3' recessed or blunt-end specific exonuclease) exonuclease is added. The exonuclease digests the blunt ended homoduplexes but not the heteroduplexes with their 3' overhang, creating big single stranded gaps in the homoduplex fragments. These can be eliminated from the reaction mix through binding to a single strand specific matrix (e.g., BND cellulose beads). The remaining heteroduplexes comprise a pool of 100% identical fragments and fragments with base pair mismatches (non-IBD fragments). A solution containing the mismatch repair enzymes mut SHL is added to the mix resulting in the nicking of mismatched heteroduplexes at a specific recognition site (GATC). These nicks are further digested by adding exo III (or an equivalent 3' recessed or blunt-end specific exonuclease) exonuclease to the reaction mix, creating big single stranded gaps in the homoduplex fragments. These can be eliminated from the reaction mix through binding to a single strand specific matrix (e.g., BND cellulose beads). The remaining fragments in the reaction mix constitute a pool of 100% identical DNA hybrids formed between the DNAs of different individuals comprising the loci responsible for the disease phenotype. These fragments can be detected and identified (e.g., by hybridisation to a DNA array representing the whole human genome). Comparison of the signals from a number of experiments in different families with the same disease phenotype allows the identification of the regions linked to disease (disease specific genome haplotype).

Example 2

Identification of Quantitative Trait Loci (QTL's) in Domestic Animals

One aim in modern agricultural animal breeding is the selection for or against certain quantitative trait phenotypes (e.g., muscle mass, milk quantity, concentration of caseine in milk for cheese production etc.). The genetic mechanisms leading to a trait are often complex with several loci implicated. These loci can be identified using our procedure. In this example genomic DNA from different animals concordant for a trait of interest (e.g., higher than average caseine concentration in milk) is restricted using a restriction endonuclease that produces on average fragments around 4 kilobases (e.g., Bam HI). To these restriction fragments a solution containing short double stranded oligonucleotides (adaptors) is added. The adaptor molecules have sequence ends complementary to the restriction site sequences to allow ligation. The adaptors are then ligated to the restriction fragments from the genomic DNAs using a common ligase (e.g., T4 ligase). The sequence of the adaptors has been chosen in a way that: a) the sequence includes the recognition site for mut HL, b) adapter dimers formed through autoligation of two adaptor molecules are self-complementary and don't compete for primers with the genomic ligation products during PCR. The adaptor carrying fragments are then separately amplified by PCR using primers that are complementary to a part of the adaptor sequence but that carry unique 5' ends. After several rounds of amplification the PCR products from the DNAs of different animals differ by their ends in respect to each other. The amplification products are then mixed, heat denatured and allowed to re-anneal using stringent hybridisation conditions (Casna et al. (1986) genomic analysis II, isolation of high molecular weight heteroduplex DNA following methylase protection and formamide PERT *Hybridization Nucleic Acids Res.* 14: 7285–7303). This results in the formation of heteroduplexes between the DNAs from different animals, with forked (single stranded) ends because of the non-complementarity of the primer sequences. In addition homoduplexes are formed by renaturation between the strands of a given animal with itself. These homoduplexes are blunt-ended. To this mixture a solution containing exo III (or an equivalent 3' recessed or blunt-end specific exonuclease) exonuclease is added. The exonuclease digests the blunt ended homoduplexes but not the heteroduplexes with their 3' overhang, creating big single stranded gaps in the homoduplex fragments. These can be eliminated from the reaction mix through binding to a single strand specific matrix (e.g., BND cellulose beads). The remaining heteroduplexes comprise a pool of 100% identical fragments and fragments with base pair mismatches (non-IBD fragments). A solution containing the mismatch repair enzymes mut SHL is added to the mix resulting in the nicking of mismatched heteroduplexes at a specific recognition site (GATC). These nicks are further digested by adding exo III (or an equivalent 3' recessed or blunt-end specific exonuclease) exonuclease to the reaction mix, creating big single stranded gaps in the homoduplex fragments. These can be eliminated from the reaction mix through binding to a single strand specific matrix (e.g., BND cellulose beads). The remaining fragments in the reaction mix constitute a pool of 100% identical DNA hybrids formed between the DNAs from different animals comprising the loci responsible for the quantitative trait of interest. These can be hybridised against an array containing a representative selection of sequences covering the whole genome of the animal. As in this case non-related animals can be used to identify the QTL's because the IBD regions should be small, i.e., a very limited number of experiments should be necessary (only one in the best case) to identify the genes responsible for the trait. The introduction of a control animal discordant for the trait of interest can further enhance the resolution of the system.

Example 3

Fine Mapping of a Disease Linked Region

Depending on the complexity and heterogeneity of a disease phenotype, the locus definition after a GMS experiment as described in example 1 may vary between several kilobases and some megabases. In the latter case further experiments must be carried out to decrease the genetic interval in which the disease gene is located. The inventive procedure can also be used to fine map the gene(s) of interest. DNA from different non-related individuals that have been shown to be linked to the same disease loci is extracted and digested by a suitable restriction endonuclease (e.g., 4 base recognition site cutter) to produce well length defined fragments. To these restriction fragments a solution containing short double stranded oligonucleotides (adaptors) is added. The adaptor molecules have sequence ends complementary to the restriction site sequences to allow ligation. The adaptors are then ligated to the restriction fragments from the genomic DNAs using a common ligase (e.g., T4 ligase). The sequence of the adaptors has been chosen in a way that: a) the sequence includes the recognition site for mut HL, b) adapter dimers formed through autoligation of two adaptor molecules are self-complementary and don't compete for primers with the genomic ligation products during PCR. The adaptor carrying fragments are then, separately for each individual, amplified by PCR using primers that are complementary to a part of the adaptor sequence and that carry unique 5' ends. After several rounds of amplification the PCR products of different individuals differ by their ends in respect to each other. The amplification products are then mixed, heat denatured and allowed to re-anneal using stringent hybridisation conditions (Casna et al. (1986) genomic analysis II, isolation of high molecular weight heteroduplex DNA following methylase protection and formamide PERT Hybridization Nucleic Acids Res. 14: 7285–7303). Depending on restrictions for the choice of the unique 5' ends for the primers, the amplification products of several individuals can be mixed, enhancing the resolution. The mixing of the PCR fragments results in the formation of heteroduplexes from the DNAs from different sources (individuals) with forked (single stranded) ends because of the non-complementarity of the primer sequences. In addition homoduplexes are formed by renaturation between the strands of one individual with itself. These homoduplexes are blunt-ended. To this mixture a solution containing exo III (or an equivalent 3' recessed or blunt-end specific exonuclease) exonuclease is added. The exonuclease digests the blunt ended homoduplexes but not the heteroduplexes with their 3' overhang, creating big single stranded gaps in the homoduplex fragments. These can be eliminated from the reaction mix through binding to a single strand specific matrix (e.g., BND cellulose beads). The remaining heteroduplexes comprise a pool of 100% identical fragments and fragments with base pair mismatches. A solution containing the mismatch repair enzymes mut SHL is added to the mix resulting in the nicking of mismatched heteroduplexes at a specific recognition site (GATC). These nicks are further digested by adding exo III (or an equivalent 3' recessed or blunt-end specific exonuclease) exonuclease to the reaction mix, creating big single stranded gaps in the homoduplex fragments. These can be eliminated from the reaction mix through binding to a single strand specific matrix (e.g., BND cellulose beads). The remaining fragments in the reaction mix constitute a pool of small 100% identical DNA hybrids formed between the DNAs of different individuals comprising the loci responsible for the disease phenotype. As there is virtually no IBD between these individuals only a very small number of relatively short fragments should be identical (this is basically a very efficient way to search for allelic association). A dense locus specific array of DNA sequences can be used to detect and identify sequences within the pool of identical DNAs. As the sequences of the array are known they can be used to directly sequence the fragments from the GMS procedure to identify open reading frames (ORF's) and the genes of interest.

Example 4

Direct Elimination of Mismatched Heteroduplexes from a Solution

Genomic DNA from at least two related individuals, with the same disease phenotype, is extracted by standard methods, e.g., phenol-chlorphorme extraction. The DNAs are separately cut with a restriction enzyme (e.g., Bam HI) to create restriction fragments with an average size around 4 kilobases. To these restriction fragments a solution containing short double stranded oligonucleotides (adaptors) is added. The adaptor molecules have sequence ends complementary to the restriction site sequences to allow ligation. The adaptors are then ligated to the restriction fragments from the genomic DNAs using a common ligase (e.g., T4 ligase). The sequence of the adaptors has been chosen in a way that: a) the sequence includes the recognition site for mut HL, b) adapter dimers formed through autoligation of two adaptor molecules are self-complementary and don't compete for primers with the genomic ligation products during PCR. The adaptor carrying fragments are then, separately for each individual, amplified by PCR using primers that are complementary to a part of the adaptor sequence and that carry unique 5' ends. After several rounds of amplification the PCR products of different individuals differ by their ends in respect to each other. The amplification products are then mixed, heat denatured and allowed to re-anneal using stringent hybridisation conditions (Casna et al. (1986) genomic analysis II, isolation of high molecular weight heteroduplex DNA following methylase protection and formamide PERT Hybridization Nucleic Acids Res. 14: 7285–7303). This results in the formation of heteroduplexes from the DNAs from different sources (individuals) with forked (single stranded) ends because of the non-complementarity of the primer sequences. In addition homoduplexes are formed by renaturation between the strands of one individual with itself. These homoduplexes are blunt-ended. To this mixture a solution containing exo III (or an equivalent 3' recessed or blunt-end specific exonuclease) exonuclease is added. The exonuclease digests the blunt ended homoduplexes but not the heteroduplexes with their 3' overhang, creating big single stranded gaps in the homoduplex fragments. These can be eliminated from the reaction mix through binding to a single strand specific matrix (e.g., BND cellulose beads). The remaining heteroduplexes comprise a pool of 100% identical fragments and fragments with base pair mismatches (non-IBD fragments).

Genomic DNA from at least two related individuals, with the same disease phenotype, is extracted by standard methods, e.g., phenol-chlorphorme extraction. The DNAs are separately cut with a restriction enzyme (e.g., Bam HI) to create restriction fragments with an average size around 4 kilobases. To these restriction fragments a solution containing short double stranded oligonucleotides (adaptors) is added. The adaptor molecules have sequence ends complementary to the restriction site sequences to allow ligation. The adaptors are then ligated to the restriction fragments from the genomic DNAs using a common ligase (e.g., T4 ligase). The sequence of the adaptors has been chosen in a way that: a) the sequence includes the recognition site for mut HL, b) adapter dimers formed through autoligation of two adaptor molecules are self-complementary and don't compete for primers with the genomic ligation products during PCR. The adaptor carrying fragments are then, separately for each individual, amplified by PCR using primers that are complementary to a part of the adaptor sequence and that carry unique 5' ends. After several rounds of amplification the PCR products of different individuals differ by their ends in respect to each other. The amplification products are then mixed, heat denatured and allowed to re-anneal using stringent hybridisation conditions (Casna et al. (1986) genomic analysis II, isolation of high molecular weight heteroduplex DNA following methylase protection and formamide PERT Hybridization Nucleic Acids Res. 14: 7285–7303). This results in the formation of heteroduplexes from the DNAs from different sources (individuals) with forked (single stranded) ends because of the non-complementarity of the primer sequences. In addition homoduplexes are formed by renaturation between the strands of one individual with itself. These homoduplexes are blunt-ended. To this mixture a solution containing exo III (or an equivalent 3' recessed or blunt-end specific exonuclease) exonuclease is added. The exonuclease digests the blunt ended homoduplexes but not the heteroduplexes with their 3' overhang, creating big single stranded gaps in the homoduplex fragments. These can be eliminated from the reaction mix through binding to a single strand specific matrix (e.g., BND cellulose beads). The remaining heteroduplexes comprise a pool of 100% identical fragments and fragments with base pair mismatches (non-IBD fragments).

A solution containing the mismatch recognizing protein mut S is added to the reaction mix. Mut S binds to the mismatched DNA at the site of the mismatch. The protein/DNA complex is then eliminated from the reaction mix by specific binding of mut S to a matrix (e.g., antibody carrying column, protein binding membrane). This procedure omits the mut LH nicking steps and the second exo III digestion as well as the need for a single strand binding matrix to eliminate the products resulting from the exonuclease digestion. The remaining identical DNA heteroduplex fragments can be detected and identified as pointed out in example 1.

What is claimed is:

1. A method comprising:
   (a) digesting separately nucleic acids from a mixture of at least two nucleic acid populations with at least one restriction enzyme;
   (b) ligating a blunt ended adaptor sequence to the restriction fragments resulting from the digestion in step (a);
   (c) amplifying adaptor-ligated restriction fragments generated in step (b) using an adaptor-specific primer to produce amplification products having different ends in respect to each population;
   (d) hybridizing the amplification products of step (c) from the different nucleic acid populations with each other to generate a mixture comprising homoduplexes and heteroduplexes;

(e) eliminating blunt ended homoduplexes from heteroduplexes having forked ends by digesting the homoduplexes with an enzyme that specifically digests blunt ended double-stranded DNA fragments;

(f) eliminating mismatched heteroduplexes by using mismatch repair enzymes; and (g) identifying, isolating or separating fully-matched heteroduplexes, thereby identifying, isolating or separating nucleic acid fragments that are identical between said at least two nucleic acid populations.

2. The method of claim 1, wherein said nucleic acid populations comprise genomic DNA populations.

3. The method of claim 2, wherein said nucleic acid populations comprise human genomic DNA populations.

4. The method of claim 3, wherein said nucleic acid populations comprise nucleic acid populations from different subjects having a common trait of interest.

5. The method of claim 1, wherein said nucleic acid populations comprise one or more selected chromosomes.

6. The method of claim 1, wherein said nucleic acid populations comprise nucleic acid populations from different sources.

7. The method of claim 1, wherein said restriction fragments are size-selected prior to said amplifying step.

8. The method of claim 1, wherein said adaptor sequence comprises a 5 base to 100 base long double-stranded DNA fragment.

9. The method of claim 1, wherein said amplifying step further comprises using a polymerase chain reaction technique.

10. The method of claim 1, wherein said primer is labelled by a technique selected from the group consisting of (a) adding a unique 5'-sequence to the primer; (b) adding a chemical activity to the primer; and (c) adding modified nucleotides into the primer, allowing one to distinguish between or among the amplification products from the nucleic acids of said at least two populations.

11. The method of claim 1, wherein said eliminating step (f) comprises incubating the hybridization mixture of step (d) with MutS, MutL, and MutH, resulting in a specific cleavage of mismatched heteroduplexes.

12. The method of claim 1, wherein the enzyme that specifically digests blunt ended double-stranded DNA fragments is exonuclease III.

13. The method of claim 1, wherein the method further comprises after step (e) a step of eliminating newly created single strands.

14. The method of claim 13, wherein said step of eliminating newly created single strands comprises binding said created single strands to a single strand specific matrix.

* * * * *